United States Patent
Florissi et al.

(10) Patent No.: US 9,361,263 B1
(45) Date of Patent: Jun. 7, 2016

(54) CO-LOCATED CLOUDS, VERTICALLY INTEGRATED CLOUDS, AND FEDERATED CLOUDS

(75) Inventors: Patricia G. S. Florissi, Briarcliff Manor, NY (US); Sudhir Vijendra, Cambridge, MA (US)

(73) Assignee: EMC Corporation, Hopkinton, MA (US)

( * ) Notice: Subject to any disclaimer, the term of this patent is extended or adjusted under 35 U.S.C. 154(b) by 0 days.

(21) Appl. No.: 13/535,796

(22) Filed: Jun. 28, 2012

Related U.S. Application Data

(63) Continuation-in-part of application No. 13/435,009, filed on Mar. 30, 2012.

(60) Provisional application No. 61/578,757, filed on Dec. 21, 2011.

(51) Int. Cl.
*G06F 15/16* (2006.01)

(52) U.S. Cl.
CPC .................... *G06F 15/161* (2013.01)

(58) Field of Classification Search
CPC ............ G06F 17/30194; G06F 15/161; G06F 21/6218; G06F 9/4856; G08B 17/00; G08B 17/10; G08B 17/11
USPC .................................................. 709/200, 217
See application file for complete search history.

(56) References Cited

U.S. PATENT DOCUMENTS

| | | | | |
|---|---|---|---|---|
| 7,552,233 | B2 * | 6/2009 | Raju ................... | G06F 12/1483 709/238 |
| 8,037,187 | B2 * | 10/2011 | Dawson ............... | G06Q 40/025 370/254 |
| 8,285,681 | B2 * | 10/2012 | Prahlad ............... | G06F 17/3002 707/640 |
| 8,352,941 | B1 * | 1/2013 | Protopopov ........ | G06F 9/45558 718/1 |
| 8,442,955 | B2 * | 5/2013 | Al Kiswany ...... | G06F 17/30233 707/610 |
| 8,478,848 | B2 * | 7/2013 | Minert .................. | G06F 9/5072 370/352 |
| 8,813,174 | B1 * | 8/2014 | Koeten ................. | H04L 41/022 709/223 |

(Continued)

OTHER PUBLICATIONS

Specification to U.S. Appl. No. 61/558,395.*

*Primary Examiner* — Anthony Mejia
(74) *Attorney, Agent, or Firm* — Krishnendu Gupta; Joseph D'Angelo

(57) ABSTRACT

A computer implemented method, program product, and apparatus for managing big data clouds comprising co-locating a big data storage cloud with a second big data cloud to enable streamlined information flow between the clouds.

20 Claims, 12 Drawing Sheets

(56) References Cited

U.S. PATENT DOCUMENTS

| | | | | |
|---|---|---|---|---|
| 2002/0046405 A1* | 4/2002 | Lahr | H04L 29/06027 | 725/87 |
| 2008/0215681 A1* | 9/2008 | Darcie | H04L 12/66 | 709/204 |
| 2009/0300719 A1* | 12/2009 | Ferris | G06F 21/606 | 726/3 |
| 2010/0198960 A1* | 8/2010 | Kirschnick | G06F 11/3414 | 709/224 |
| 2011/0167469 A1* | 7/2011 | Letca | G06F 21/6218 | 726/1 |
| 2012/0030356 A1* | 2/2012 | Fletcher | G06F 9/5094 | 709/226 |
| 2012/0047266 A1* | 2/2012 | Minert | G06F 9/5072 | 709/226 |
| 2012/0124194 A1* | 5/2012 | Shouraboura | G06F 9/5066 | 709/224 |
| 2012/0131217 A1* | 5/2012 | Delorme | G06Q 10/06 | 709/230 |
| 2012/0137002 A1* | 5/2012 | Ferris | G06F 9/5072 | 709/226 |
| 2012/0324112 A1* | 12/2012 | Dow | G06F 9/5077 | 709/226 |
| 2013/0007091 A1* | 1/2013 | Rao | G06F 17/30212 | 709/201 |
| 2013/0054634 A1* | 2/2013 | Chakraborty | G06F 17/30206 | 707/769 |
| 2013/0124483 A1* | 5/2013 | Furuhashi | G06F 17/30315 | 707/661 |
| 2013/0166568 A1* | 6/2013 | Binkert | G06F 17/30911 | 707/741 |
| 2013/0339108 A1* | 12/2013 | Ryder | G06Q 10/02 | 705/14.1 |
| 2014/0201218 A1* | 7/2014 | Catalano | G06F 8/60 | 707/748 |

* cited by examiner

CO-LOCATED CLOUDS, VERTICALLY INTEGRATED CLOUDS, AND FEDERATED CLOUDS

RELATED APPLICATIONS AND PRIORITY CLAIM

This application is a Continuation-in-Part of U.S. patent application Ser. No. 13/435,009 entitled "BIOINFORMATICS CLOUDS AND BIG DATA ARCHITECTURE" filed on Mar. 30, 2012, the contents and teachings of which are incorporated herein by reference in their entirety, which application claims the benefit of U.S. Provisional Patent Application Ser. No. 61/578,757 entitled "BIOINFORMATICS CLOUDS AND BIG DATA ARCHITECTURE" filed on Dec. 21, 2011, the contents and teachings of which are incorporated herein by reference in their entirety.

This application is related to U.S. patent application Ser. No. 13/535,684 entitled "WORLDWIDE DISTRIBUTED FILE SYSTEM MODEL", Ser. No. 13/535,696 entitled "WORLDWIDE DISTRIBUTED ARCHITECTURE MODEL AND MANAGEMENT", Ser. No. 13/535,712 entitled "EXECUTION FRAMEWORK FOR A DISTRIBUTED FILE SYSTEM", Ser. No. 13/535,731 entitled "PARALLEL MODELING AND EXECUTION FRAMEWORK FOR DISTRIBUTED COMPUTATION AND FILE SYSTEM ACCESS", Ser. No. 13/535,814 entitled "WORLDWIDE DISTRIBUTED JOB AND TASKS COMPUTATIONAL MODEL", Ser. No. 13/535,744 entitled "ADDRESSING MECHANISM FOR DATA AT WORLD WIDE SCALE", Ser. No. 13/535,760 entitled "SCALABLE METHOD FOR OPTIMIZING INFORMATION PATHWAY", and Ser. No. 13/535,821 entitled "DISTRIBUTED PLATFORM AS A SERVICE", filed on even date herewith, the contents and teachings of which are incorporated herein by reference in their entirety.

A portion of the disclosure of this patent document may contain command formats and other computer language listings, all of which are subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This invention relates to Big Data.

BACKGROUND

The amount of data in our world has been exploding. Companies capture trillions of bytes of information about their customers, suppliers, and operations, and millions of networked sensors are being embedded in the physical world in devices such as mobile phones and automobiles, sensing, creating, and communicating data. Multimedia and individuals with smartphones and on social network sites will continue to fuel exponential growth. Yet, the impact this growing amount of data will have is unclear.

SUMMARY

A computer implemented method, program product, and apparatus for managing big data clouds comprising co-locating a big data storage cloud with a second big data cloud to enable streamlined information flow between the clouds.

DESCRIPTION OF DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every figure. The drawings are not necessarily to scale, emphasis instead being placed upon illustrating embodiments, principles, and concepts. Thus, features and advantages of the present disclosure will become more apparent from the following detailed description of exemplary embodiments thereof taken in conjunction with the accompanying drawings in which:

DETAILED DESCRIPTION

Figure 1:
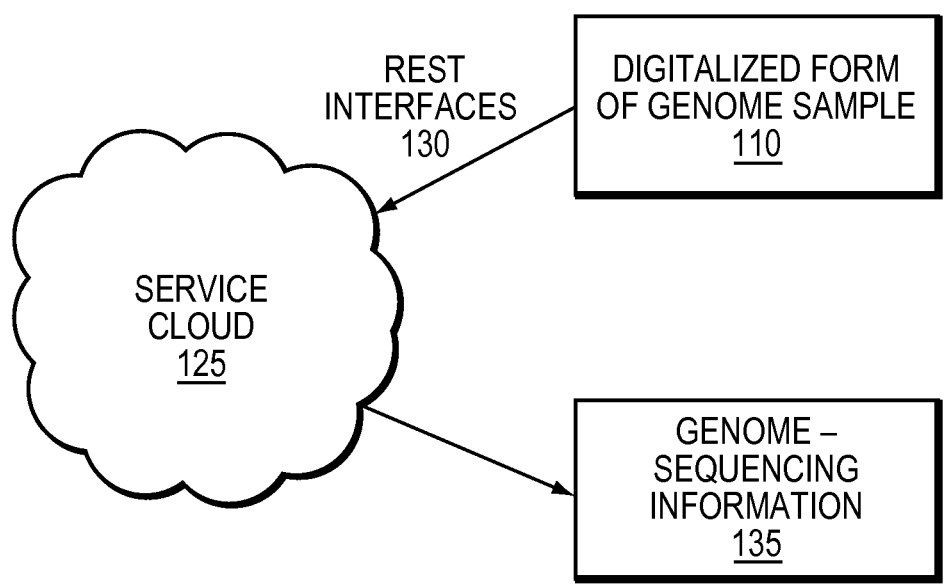
FIG. 1 is a simplified illustration of a cloud providing services over Representational State Transfer (REST) interfaces, in accordance with an embodiment of the present disclosure.

In certain embodiments, this disclosure provides a set of Cloud designs which may reduce data movement for big data system. In certain embodiments, the current disclosure may provide a streamlined production line. In some embodiments, the current disclosure may enable creating an efficient and integrated pipeline for Big Data flow. In other embodiments, the current disclosure may enable accelerating the commoditization of Big Data acquisition and the use of analytics to drive insight.

In certain embodiments, the current disclosure may create efficiencies for big data sets including bioinformatics (e.g., Genomics, Proteomics, Metabolonics, Metagenomics), smart energy with the adoption of Smart Meters, and exploration and production of hard to find, deep Oil & Gas.

In certain embodiments, the current disclosure may enable co-location of several types of "as a service" analysis for Big data sets may streamline information flow. In other embodiments, vertically integrated big data clouds may be enabled that reduces, minimizes and may eliminate data staging from one type of storage to another. In some embodiments, the current disclosure may enable federation of clouds, which may enable analytics to be executed and orchestrated at a World Wide Scale. In further embodiments, preference may be given to move analytic applications closer to the source of data, as opposed to moving data to where the analytics are.

In some embodiments, the current disclosure describes the design of a Platform as a Service that may capture meta-information on the data stored at the Information Infrastructure layer. In certain embodiments, this metadata may be useful for capture and processing of Bioinformatics Big Data Sets. In other embodiments, a Platform Layer is presented which may includes application, tools and other computational activities to mine, organize, and analyze the data stored in an Infrastructure Layer. In at least one embodiment, the current disclosure enables additional insights into Big Data. In further embodiments, the insights available may be enabled in a standard format.

In certain embodiments, insights obtained from the Big Data may be referred to as Big Meta Data. In some embodiments, Big Meta Data may be created, maintained, and managed at the Platform Layer. In further embodiments, Big Meta Data my leverage the underlying Cloud Information Infrastructure. In still further embodiments, Big Meta Data may be stored, archived, protected, backed-up, accessed and further analyzed alongside the Big Data set to which it pertains. In an embodiment, Platform as a Service Layer may benefit from principles of Data Locality and Data Accessibility by being closer to the source of the Data. In certain embodiments, platform as a service layer may utilize "non-utilized" processing cycles available at the Cloud Infrastructure Layer to mine data.

In some embodiments, "Big Data" may refer to a dataset that has a size, volume, analytical requirements, or structure demands larger than typical software tools may capture, store, manage, and analyze. In certain embodiments, "Big Data" may refer to a dataset that has a combination of attributes, such as size, volume, structure, or analytical requirements, with which typical software tools may not be able to work. In most embodiments, big data is not defined in terms of being larger than a certain number of terabytes rather, as technology advances over time, the size of datasets that qualify as big data may also increase. In certain embodiments, data transfer speed and no of transactions may also attributes of Big Data.

In further embodiments, the definition of "Big Data" may vary by sector or industry, depending on what kinds of software tools are commonly available and what sizes of datasets are common in a particular industry. Big Data may refer to data from Digital Pathology, data from seismological surveys, data from the financial industry, and other types of data sets that are generally too large, for example in size or number of transactions, to be modeled an analyzed with conventional techniques.

Typically, organizations and business units share IT services, which may result in the creation of Big Data. Generally, the network, apps, and servers are shared and/or dedicated in many instances. Usually, of cloud and Big Data models and analytic platforms provide opportunities for the storage business. However, conventional file sizes vary depending on the verticals, domains and type of data. Conventionally solutions provide a good infrastructure to host files that are large in size, but not for smaller files.

For example, a conventional cluster type architecture for big data assumes a flat commodity world, where processing cores and disk drives are cheap and abundant, even though they may and will fail often, applications are computing and data intensive, where computations may need to be done over the entire data set; and in processing Big Data, transfer time becomes the new bottleneck. Traditionally, a Cluster architecture may be based on a set of very simple components and assumes that there are hundreds or thousands of these components together, a node may have a set of processing cores attached to a set of disks, a rack may have a stack of nodes, and a cluster may have a group of racks. Conventionally, within the context of a Cluster, Big Data is typically divided into equal size blocks and the blocks are distributed across the disks in the nodes. Usually, the data in each node may processed by the processing cores in the node providing Data Locality where the data is collocated with the computing node.

Typically, distributed file systems may provide data in a data center to be split between nodes. Generally, a distributed file system may split, scatter, replicate and manage data across the nodes in a data center. Typically, a file system may be a distributed file system when it manages the storage across a network of machines and the files are distributed across several nodes, in the same or different racks or clusters. Conventionally, map reduce may be a computational mechanism to orchestrate the computation by dividing tasks, collecting and re-distributing intermediate results, and managing failures across all nodes in the data center. In certain embodiments, the current techniques may enable data to be split between nodes. In other embodiments, the current techniques may enable computation on data that has been split between nodes.

Conventionally, a distributed file system may a set of equal size blocks. Typically these blocks may be multiples of a simple multiplier, such as 512 kb. Generally, file blocks may be the unit used to distribute parts of a file across disks in nodes. Usually, as disks in a node and nodes in a rack may fail, the same file block may be stored on multiple nodes across the cluster. Typically, the number of copies may be configured. Usually, the Name Node may decide in which disk each one of the copies of each one of the File Blocks may reside and may keep track of all that information in local tables in its local disks. Conventionally, when a node fails, the Name Node may identify the file blocks that have been affected; may retrieve copies of these file blocks from other healthy nodes; may find new nodes to store another copy of them, may store these other copies; and may update this information in its tables. Typically, when an application needs to read a file, may connects to the Name Node to get the addresses for the disk blocks where the file blocks are and the application may read these blocks directly without going through the Name Node anymore.

Generally, Big Data is Multi Structured and may be conventionally stored, analyzed and managed each type of information in a number of different ways. In some embodiments, structured data may be stored in Block based, SQL, and RDBMS type databases. In other embodiments, semi-structured data may be stored in XML Data Files, in File Based systems, and in Hadoop Map Reduce. In further embodiments, quasi-structured data may be data containing some inconsistencies in data values and formats, e.g., Web clickstream data. In some embodiments, unstructured data may be text documents that could be subject to analytics over text or numbers such as file based data, Hadoop MapReduce, and HDFS data. In other embodiments, unstructured data may be images and video such as file based data, and data streamlined with technologies such as MapReduce, or Scale Out NAS data. Typically, it may be difficult to process information stored in all different formats, cross-analyze content, or visualize and gain insight into the important information spread all over the different formats.

As used herein, for simplicity, a framework for Massive Parallel Processing (MPP) within the delimiters of a Cluster or data set may be referred to as Hadoop by way of example, however any framework may be used and the current techniques are not limited to use with Hadoop. Generally, the Hadoop framework focuses on Massive Parallel Processing (MPP) within the delimiters of a Cluster or data set. Often, Hadoop may be utilized in an attempt to analyze Big Data.

Usually, Hadoop assumes that data or Big Data has been transferred to a single cluster and has been evenly distributed across the nodes of the cluster. Typically, Hadoop does not enable analysis of data across multiple clusters. Conventionally, different parts of the Big Data may reside on different clusters potentially spread across different clouds. Usually, a retail enterprise may need to analyze its sales transactions over the last 5 years, but it may store last four years' transactions in a Public Cloud while retaining the last 12 months in its own Private Cloud. Generally, the enterprise does not have the storage, processing capacity or bandwidth, to repatriate the last four years worth of Big Data to its private cloud. In an embodiment, the current disclosure enables management of big data sets where the content may exist across numerous clouds or data storage centers. Generally, with respect to the data, there may be two architectural frameworks. Conventional architecture design may assume that there are three main types of hardware resources to be managed, servers, enclosing very expensive processors that should not be idle at any moment in time, storage Arrays, enclosing drives of different performance and capacity ranging from Solid State Drive (SSD) to Fiber Channel and SATA, and Storage Area Network (SAN), connecting a set of servers to a set of storage arrays. Generally, this architecture may assumes that most applications are "computing intensive" meaning that there may be high demand for processing power that performs computation on a subset of all the data available for the application, which may be transferred across the SAN to the servers.

In some embodiments, World Wide Hadoop (WWH) or other big data processing methodologies may enable Massive Parallel Processing (MPP) to be executed across multiple clusters, and clouds without requiring one or more Big Data sets to be located at the same location. In certain embodiments, WWH may have a layer of orchestration on top of Hadoop or a similar architecture that manages the flow of operations across clusters of nodes. In other embodiments, the clusters maybe separate across metro or worldwide distances. In further embodiments, the current techniques may enable World Wide Hadoop (WWH) to enable Genome Wide Analysis (GWA) of Genomes that reside on different Genome Banks, one located in NY and another located in MA.

In certain embodiments, World Wide Hadoop may be applied where big data clouds exist. In certain embodiments, clouds may be extension of the other clouds. In other embodiments, clouds may be an independent cloud. In further embodiments, clouds may be providing an analysis services to other clouds. In some embodiments, the big data clouds may exchange raw data or analyze data for further processing.

In certain embodiments, the domain expertise, open data, open science data, analysis etc, may come from different geographic locations and different clouds may host the respective big data. In at least some embodiments, the federation among big data clouds may present an internet infrastructure challenge.

In some embodiments, factors like cost and bandwidth limit may affect the big data Hadoop deployment federation. In certain embodiments, the current techniques may model Hadoop environments. In other embodiments, the current techniques may re-define roles of the Hadoop components in the Hadoop clusters. In certain embodiments, Massive Parallel Processing may be enabled across clouds. In some embodiments, WWH concepts apply where there are many big data clouds, and the clouds may need to either exchange raw data or analyze data for further processing. In some embodiments, as used herein, a cluster may be used interchangeably with a data center.

The following may be helpful in understanding the specification and claims:

Acquisition Cloud: may define a set of services to generate, create, obtain, accumulate or aggregate data. In certain embodiments, this data can be input by humans filling out forms. In other embodiments, this data may be delivered by devices responsible for creation, ingestion or aggregation of information in digital format. In most embodiments, a user in the loop may be involved to operate such devices and to add data to the information acquired. In some embodiments, an Acquisition Cloud may take as input non-digital information, such as blood samples, body tissues or glass slides, and create a digital representation of the data. In some embodiments, the representation may have a series of digital files for each non-digital input. In other embodiments, the representation may contain additional information that was inserted, such as annotation to the data capturing information acquired or observed during the process of ingestion. In at least one embodiment, the representation may contain historical information logging time and date of milestones in the acquisition process, and identity information creating a link and a data lineage from the data to its origin and originators.

Sequencing as a Service: may be an acquisition cloud with a set of genome sequencing device that receive as input a wet sample (e.g., blood sample or tissue) and generate a digital image of it;

Smart Metering as a Service: may be an acquisition cloud with a set of computing and storage devices that receive the measurements done by the Smart Meters located on every real-state property (residence, business or otherwise), and aggregates this information for compliance, archival, billing, reporting, analytics or other functions.

Pre-stack Seismic Data as a Service: may be an acquisition cloud with a set of tape readers, computing and storage devices that receive loads and loads of tapes, reads the content of the tapes and stores the data into disk for permanent storage, transmission, compliance, reporting, archival, analytics, visualization or other functions.

Social & Blog Data Cloud as a Service: may be an acquisition cloud with a set of applications that constantly monitor and read sites where social events, blog posts and other types of information are published or exchanged among friends, communities, social groups, network users, or individuals with similar interest, and aggregates this content to be accessed by other entities.

Storage Cloud: may define a set of services to store, archive, back up, provide access, protect, secure and manage data. A Storage Cloud may take as input digital information coming from many sources, including Acquisition Clouds, massive data transfers from other storage devices or other Storage Clouds, applications and human entered content.

Processing Cloud: may define a set of services to process or analyze data. In certain embodiments, before processing, information may be uploaded in the Processing Cloud, where data may be processed and the results are provided back. In some embodiments, there may be APIs made available to input information and to retrieve information as well.

Visualization Cloud: may define services to allow the visualization of data, including services such as printing services, or displaying services through higher quality displays (e.g., Flat screens, billboards, etc).

Collaboration and Sharing Cloud: may define services to allow data to be shared among people of common interest. In certain embodiments, a collaboration and sharing cloud may store documents or files. In other embodiments, collaboration and sharing clouds may store for users medical images and give doctors and other interested parties access to the site to view the medical images;

Manufacturing Cloud: may define services to allow the transformation or conversion of digital information back into non digital one. In an embodiment, a manufacturing cloud may enable printing of information using 3-D printers;

Archival Cloud: may define a set of services to store, protect and archive data. In certain embodiments, the service of an archival cloud may assume that the data has been acquired, gathered, processed, utilized or fulfilled. In some embodiments, an archival cloud may be used for permanent storage for compliance or archival purposes.

Back-up or Disaster Recovery Cloud: may define a set of services to provide alternative storage for data stored in another Cloud. In certain embodiments a back-up or disaster recover cloud may be considered a secondary storage place to retrieve information in case the primary source is damaged or no longer available.

The following list of acronyms may be useful in understanding the terms use here in:
WW—World Wide
WWH—World Wide Hadoop
DNN—Distributed Name Node
DDN—Distributed Data Node
MPP—Massively Parallel Processing
SSD—Solid State Drive
GWA—Genome Wide Analysis
FS—File System
WWDFS—World Wide Distributed File System
DFS—Distributed File System
HDFS—Hadoop Distributed File System
WWHDFS—World Wide Hadoop Distributed File System
WWF—World Wide File
WWN—World Wide Name
WWFN—World Wide File Name
WWS—World Wide Scale
WWJT—World Wide Job Tracker
WWTT—World Wide Task Tracker
WWA—World Wide Addressing
WWD—World Wide Data Data Model In most embodiments a data model or modeling structure may be used to process data across clusters. In most embodiments, the data model may enable representation of multiple data sets. In certain embodiments, this model may include data notes, data clusters, data centers, clouds, and skies.

In most embodiments, the classes, objects, and representations referenced herein may be an extension of known distributed system models, such as the EMC/Smarts Common Information Model (ICIM), or similarly defined or pre-existing CIM-based model and adapted for the environmental distributed system, as will be discussed. EMC and SMARTS are trademarks of EMC Corporation, Inc., having a principle place of business in Hopkinton, Ma, USA. This exemplary model is an extension of the DMTF/SMI model. Model based system representation is discussed in commonly-owned U.S. patent application Ser. No. 11/263,689, filed Nov. 1, 2005, and Ser. No. 11/034,192, filed Jan. 12, 2005 and U.S. Pat. Nos. 5,528,516; 5,661,668; 6,249,755 and 6,868,367, and 7,003,433, the contents of all of which are hereby incorporated by reference. An example of a Big Data Set may be found in commonly-owned U.S. patent application Ser. No. 12/977,680, filed Dec. 23, 2010, entitled "INFORMATION AWARE DIFFERENTIAL STRIPING" the contents of which are hereby incorporated by reference. An example of modeling Big Data Set may be found in commonly-owned U.S. patent application Ser. No. 13/249,330, filed Sep. 30, 2011, entitled "MODELING BIG DATA" the contents of which are hereby incorporated by reference. An example of analyzing Big Data Set may be found in commonly-owned U.S. patent application Ser. No. 13/249,335, filed Sep. 30, 2011, entitled "ANALYZING BIG DATA" the contents of which are hereby incorporated by reference.

Generally, referred-to US patents and patent applications disclose modeling of distributed systems by defining a plurality of network configuration non-specific representations of types of components (elements or devices) managed in a network and a plurality of network configuration non-specific representations of relations among the types of managed components and problems and symptoms associated with the components and the relationships. The configuration non-specific representations of components and relationships may be correlated with a specific Big Data set for which the associated managed component problems may propagate through the analyzed system and the symptoms associated with the data set may be detected an analyzed. An analysis of the symptoms detected may be performed to determine the root cause—i.e., the source of the problem—of the observed symptoms. Other analysis, such as impact, fault detection, fault monitoring, performance, congestion, connectivity, interface failure, in addition to root-cause analysis, may similarly be performed based on the model principles described herein.

Clouds

In a particular embodiment, information may flow from or is staged in an Acquisition Cloud to Storage Cloud. In another embodiment, information may flow form a Processing Cloud to a Visualization Cloud. In a further embodiment, information may flow form a visualization cloud to Collaboration and Sharing Cloud. In a still further embodiment, information may flow from a collaboration and sharing cloud to a Manufacturing Cloud. In an alternative embodiment, information may flow from a Manufacturing Cloud to an Archival Cloud.

In certain embodiments, the information in any of the clouds may be replicated into a Back-Up and/or Disaster Recovery Cloud. In some embodiments, the decision to back-up the data may depend on the nature of the data. In other embodiments, the decision to back up the data may depend on the data requirements. In further embodiments, the decision to back-up the data may depend on the value of the data as an asset. In at least one embodiment, the decision to back-up the data may depend on the Governance, Risk and Compliance (GRC) requirements for the data. In certain embodiments, the GRC function may be located on a separate cloud. In most embodiments, the GRC cloud may be geographically located in the region where a specific geo region to ensure compliance with that region's GRC requirements. In most embodiments, the decision to back-up the data may depend on the ability of the system to re-produce the data.

Generally, there are economies of scale within the Clouds (intra-cloud), there is typically few or no economies of scale inter-cloud. In certain embodiments, movement between clouds may encounter time delays for staging the data from one cloud to another. In other embodiments, as monetary cost for services may be paid for individually users may not benefit from discounts of using or buying multiple services from same vendor or at the same time or more of a longer term contract. In further embodiments, there may be added complexity in managing data across several, potentially desperate Clouds. In an embodiment, there may be complexity in managing relationships to potentially separate vendors, with different contracts. In at least some embodiments, there may be complexity in potentially consolidating data that belongs to several clouds. In an embodiment, there may be several Acquisition Clouds collecting and gathering data that may be stored in a different Storage Cloud. In other embodiments, data from several Storage Clouds may be processed in another Cloud and the data may need to be consolidated in a Processing Cloud.

Cloud Co-Location

In certain embodiments, the current disclosure may enable physical co-location of Clouds. In other embodiments, the current disclosure may enable minimizing the distance between clouds. In some embodiments, information flow may be streamlined from several clouds. In an embodiment, this may enable the information to flow faster. In other embodiments, this may enable the information to transfer through higher speed means of digital communication. In another embodiment, the co-located clouds may leverage local connection cables. In at least one embodiment, co-location of clouds may improve security, minimize risks in the transmission of data, and minimize costs. In other embodiments, Cloud Co-location may provide many benefits high bandwidth and fast transmission of information. In most embodiments, co-located clouds may reduce, minimize, or eliminate data staging from one type of Cloud or storage to another.

In a particular embodiment, Genome Sequencing Acquisition Cloud may be co-located with a Storage Cloud. In this embodiment, information flows directly from the sequencing machine, where the sequences are generated, into the Storage Cloud where the sequences may be stored permanently. In this embodiment, the co-location avoids the need for intermediate storage of data in disks or CDs, the physical or digital transportation of these media, and the uploading of this information into disks.

In another embodiment, a Storage cloud and an Archival Cloud may be co-located. In this embodiment, information flows from the Storage Cloud into the Archival Cloud seamlessly. In another embodiment, a Digital Pathology Images Acquisition Cloud may be co-located with a Storage Cloud and Collaboration Cloud. In this embodiment, a digital pathology image is generated and is transmitted to a co-located Storage Cloud and to a Collaboration Cloud. In this embodiment, at the Collaboration Cloud, the digital pathology images may be viewed and shared by many sources.

Refer now to the example embodiment of FIG. 1. In the example embodiment of FIG. 1, a digitalized form of genome sample 110 is sent to service cloud 125 via representational state transfer (rest) interface 140. The service cloud 125, which may have both storage and analytical capabilities co-located, performs genome sequencing on the genome sample and provides the genome sequencing information 135 through rest interfaces.

Figure 2:
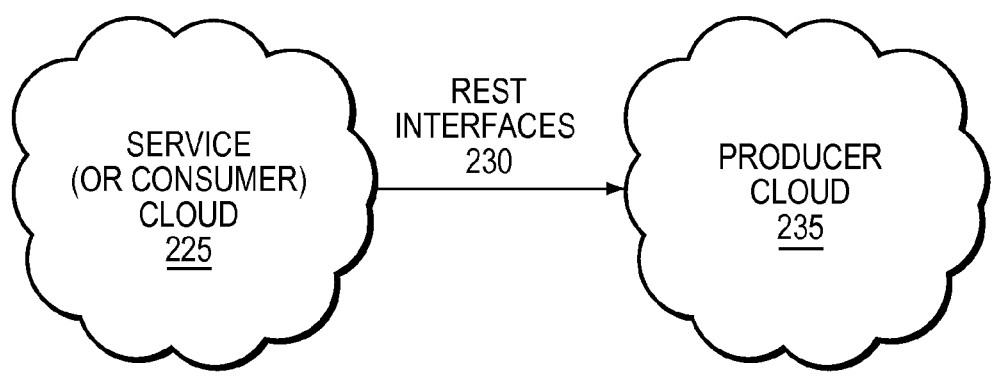
FIG. 2 is an alternative simplified illustration of a cloud providing services over rest interfaces, in accordance with an embodiment of the present disclosure.

Refer now to the example embodiment of FIG. 2. In this embodiment producer cloud 235 is connected to service/consumer cloud 225 via Rest Interfaces 230.

Vertically Integrated Clouds

In some embodiments, clouds may be vertically integration to streamline the information flow. In certain embodiments, vertical integration may enable minimization or eliminating data staging. In at least some embodiments, vertical integration may be implemented as a vertical stack of Clouds. In other embodiments, vertical integration may be implemented as a Network of Clouds. In at least one embodiment, vertical integration of clouds may enable Clouds to have access to a shared media where information is posted and broadcast.

In certain embodiments, vertical integration may enable Clouds to listen and access information of the other clouds. In further embodiments, mechanisms may be deployed to share the information, without requiring broadcast such as a common service architecture or a federation of the clouds. In further embodiments, Clouds may subscribe to types of data. In other embodiments, clouds may notify the source of the data and the source of the data may notify the subscribing cloud when information becomes available.

In some embodiments, directly attaching devices in the Acquisition Cloud to devices in the Storage Cloud may enable digital information to lent or be ingested in the Storage Cloud as soon as it is created or generated in the Acquisition Cloud. In certain embodiment, this may be illustrated by connecting genome sequencing devices into Storage devices and charging customers a different price for the Acquisition together with the Storage.

In some embodiments, devices in a network may be connected to the Acquisition Cloud which may enable the data to be shared and broadcast to devices in multiple Clouds, including a Storage Cloud and an Archival Cloud. In other embodiments, directly attaching Acquisition, Storage and Processing (Analytics) Clouds, may elimination information staging from inception of the data to analysis of the data. In at least one embodiment, a Storage Cloud, an Acquisition Cloud and an Analytics Cloud may be linked through federation of the clouds. In some embodiments, the information generated or created by the Acquisition Cloud may be stored in the Storage Cloud, with no intermediate storage media. In other embodiments, an Analytics Cloud may access/retrieve data directly from the Storage Cloud into its main memory where the analysis is performed without the need for staging.

Cloud Federation

In certain embodiments, geographically dispersed clouds may be connected through federation, for example by a digital network. In some embodiments, a federated cloud may enable execution and orchestration activities across Clouds. In at least some embodiments, the federation may be on World Wide Scale enabling moving, analytics, and processing of data closer to the source of data. In further embodiments, federation may remove any need to move data where the processing resources are.

In an embodiment, federation may enable execution against data that resides in different Clouds. In further embodiments, the world wide data, which may be classified as Big Data, may be locked in the Clouds where they were Acquired, Stored, Processed or otherwise Managed. In most embodiments, instead of moving this data, federation may enable a single federated cloud from the individual Clouds have Co-located Clouds and/or Vertically Integrated Clouds.

Figure 3:
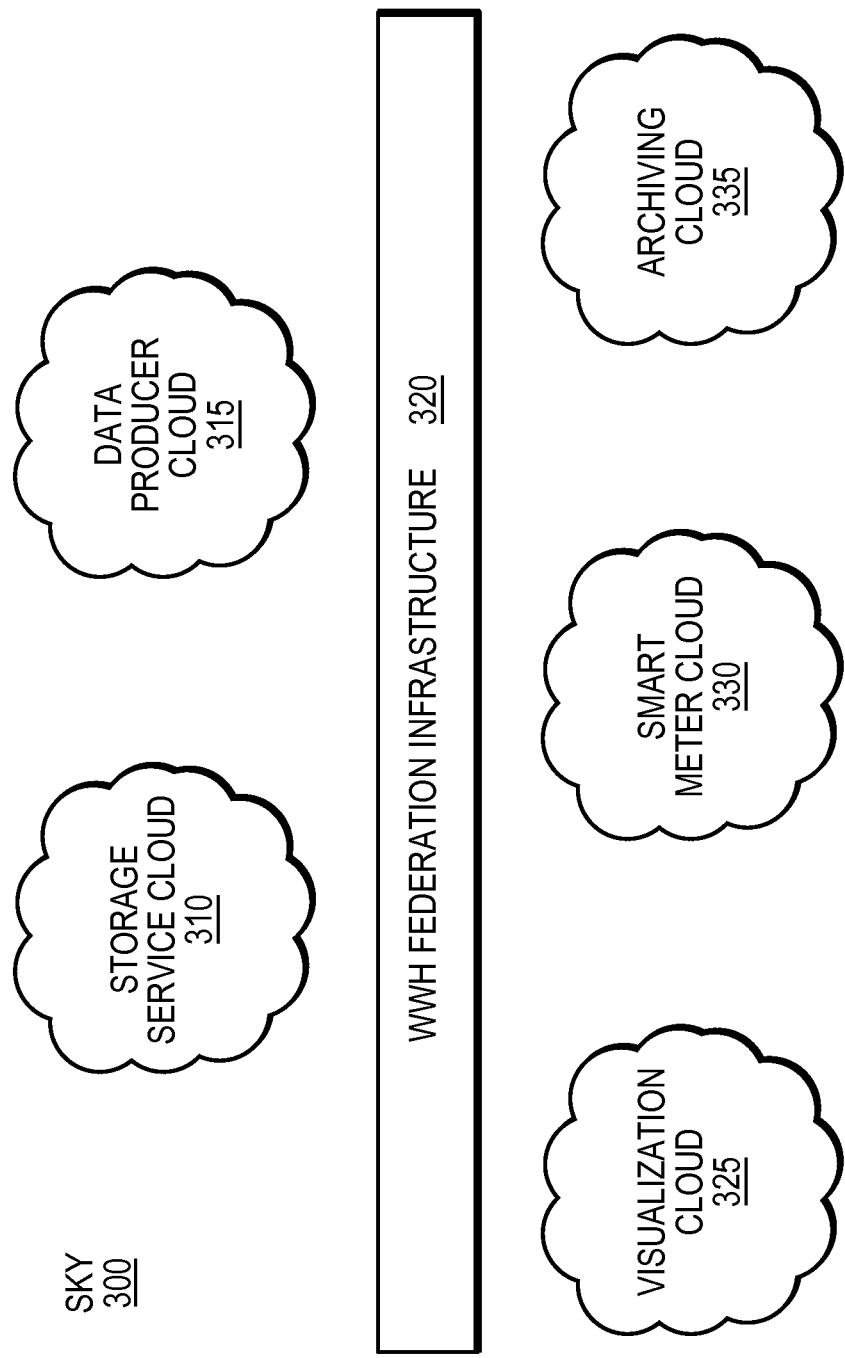
FIG. 3 is a simplified illustration of Clouds and Services over a WWH Federation Infrastructure, in accordance with an embodiment of the present disclosure.

Refer now to the example embodiment of FIG. 3. FIG. 3 illustrates sky 300 with five clouds 310, 315, 325, 330, and 335, connected via WWH federation infrastructure 330. Each cloud in Sky 300 may communicate via WW Federation Infrastructure 320. The clouds may subscribe to information from other clouds and publish information for consumption by other clouds via WW Federation Infrastructure. In this embodiment, storage service cloud 310 may be located with data producer cloud 315. Visualization cloud 325, smart meter cloud 330, and archiving cloud 335 may also be co-located.

Figure 4:
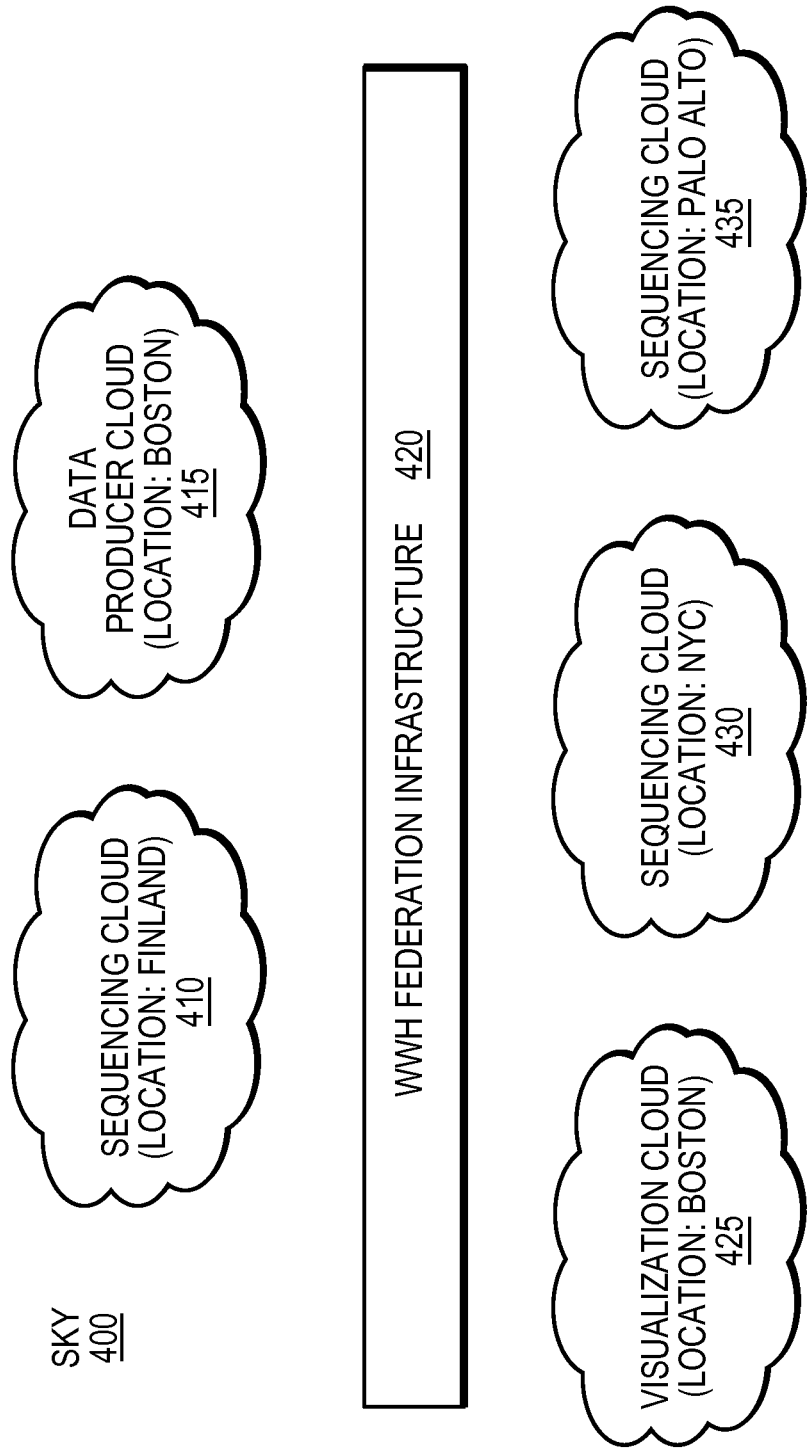
FIG. 4 is a simplified illustration of Co-located Clouds as one Service over a WWH Federation Infrastructure, in accordance with an embodiment of the present disclosure.

Refer now to the example embodiment of FIG. 4. In the example embodiment of FIG. 4, there is sky 400 with 5 clouds, 4 of which are located in different geographic locations. The clouds are presented as a single service through WW Federation Infrastructure 420. Sequencing cloud 410 in Finland may process data produced by cloud 415 located in Boston. Visualization cloud 425 in Boston may receive information from the sequencing cloud 425 in Finland. As well, sequencing clouds 430 and 435, in New York and Palo Alto, respectively, may also receive data from producer cloud 415 via federation infrastructure 420. Visualization cloud 523 may also display information from clouds 430 and 435.

Figure 5:
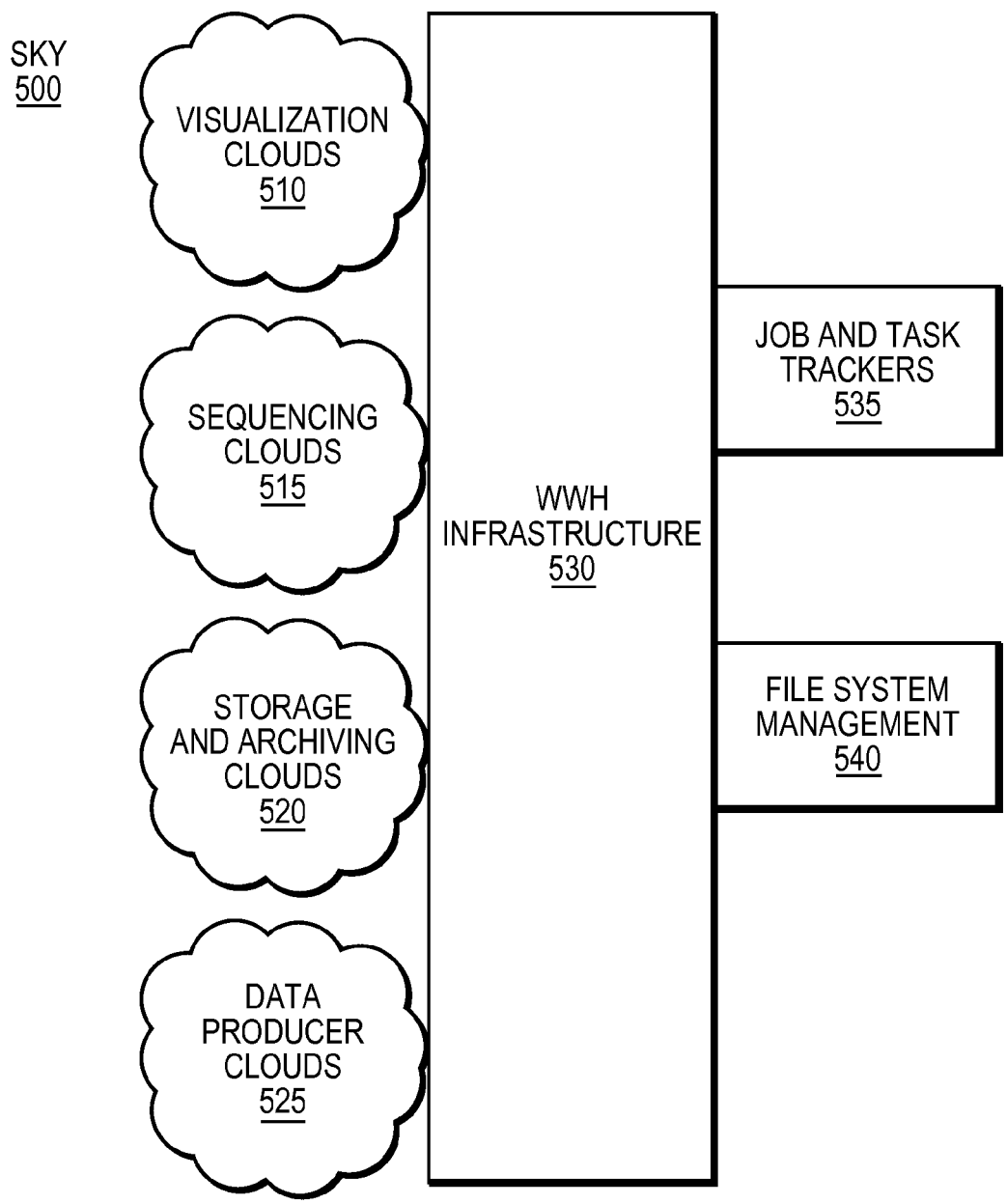
FIG. 5 is a simplified illustration of Vertically Integrated Clouds—Decoupled services over WWH Infrastructure, in accordance with an embodiment of the present disclosure.

Refer now to the example embodiment of FIG. 5 which illustrates vertically integrated clouds providing decouple services over a WWH infrastructure. In Sky 300, there are four cloud types, visualization clouds 510, sequencing clouds 515, storage and archiving clouds 520 and data producer clouds 525. These cloud types are connected via WWH Infrastructure 530 to job and task trackers 535 and file system management 540.

Figure 6:
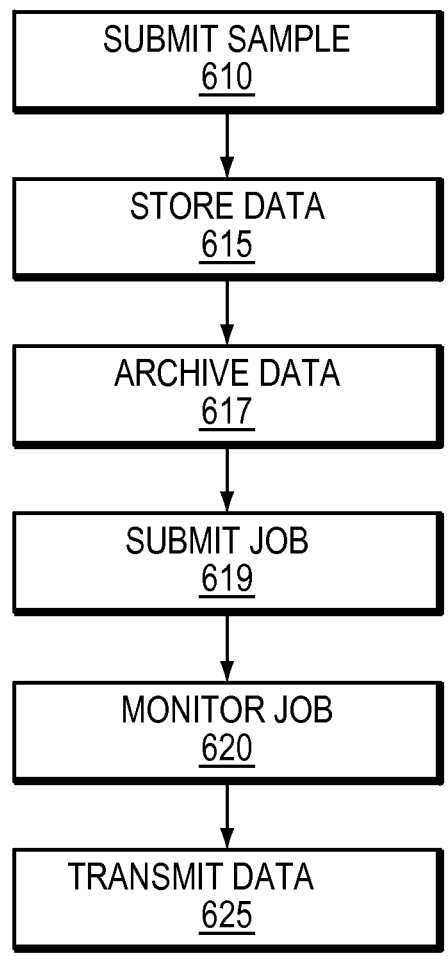
FIG. 6 is a simplified method for Requesting a service from a cloud, in accordance with an embodiment of the present disclosure.

Refer now to the example embodiment of FIG. 6, which illustrates requesting a service from a cloud located on WWH infrastructure. A user submits a digitalized wet pathology sample for scientific genomic related data analysis from a private cloud which is connected to WWH infrastructure (step 610). WWH infrastructure (specifically WW name node server) stores the data in the storage cloud (step 615) WWH Infrastructure archives the data in an archive cloud (step 617). WWH Infrastructure submits the job to sequencing cloud (step 619). WWH Job/Task trackers monitor the job and the reduce cloud reduces the result (step 620). WWH name node starts transmitting data using http and/or https protocols back to user in the data producer cloud (step 625). In certain embodiments, an end of data message is sent at the end.

Platform as a Service

In certain embodiments, the current disclosure may enable platform as a Service for Creation and Management of Open Big Data Big Meta Data. In certain embodiments, the platform as a service may enable management tools such as a file system for the data, map reduce for jobs, service tools and API support. In other embodiments, platform as a service may provide services such as Infrastructure Planning, Back up and Achieving, Encryption, and API Support. In some embodiments, platform as a service may provide management Tools such as FS management tools use WWH file system model, FS management tools provides both GUI and API access at the PaaS layer, FS tools use FS mgmt commands or operations to perform infrastructure level calls, such as Read, Create, Delete, Remove, Open and Insert.

In some embodiments, WWH Management Tools may be implemented. In an embodiment, these tools may include map Reduce management tools which may use a WWH computational model. In other embodiments, Map Reduce management tools may provides both GUI and API access at the PaaS layer to manage WWH jobs/tasks. In at least one embodiment, Map Reduce tools may use management commands or operations to perform infrastructure level calls. In certain embodiments, management tools may include commands such as Start job/task, Terminate job/task, Run job/task. In a further embodiment, the management tools may provide Reduce functions to allocate reduce data nodes.

Refer now to the example embodiment of FIG. 5, which illustrates a WWH FS management tool center. Sky 715 has 5 clouds and WWH Federation Infrastructure 720. WW FS Management Center and console 710 communicates through WWH Federation infrastructure 720 with a NYC FS 725, Boston FS 730, UAE FS 735 and Europe FS 715. WWH FS Management center and console 710 serves as a central means to manage data and implement jobs within these set of clouds.

In certain embodiments, the WWH framework may provide infrastructure services from the management station and console. In certain embodiments the infrastructures may include a WWH Back up Service. In other embodiments, the WWH framework may include local and remote back-up. In some embodiments, the WWH framework may provide a set of back up jobs to perform back up tasks. In at least some embodiments, the WWH infrastructure may enable a WWH Charge Back Service. In an embodiment, WWH PaaS may provide many services that are charged. In certain embodiments, the charge service may be based on data services. In another embodiment, the charges may be on Data In/Out Transfer. In a further embodiment, the charge may be based on optimization and encryption levels. In at least some embodiments, the WWH infrastructure services may provide API and console/GUI access.

Figure 8:
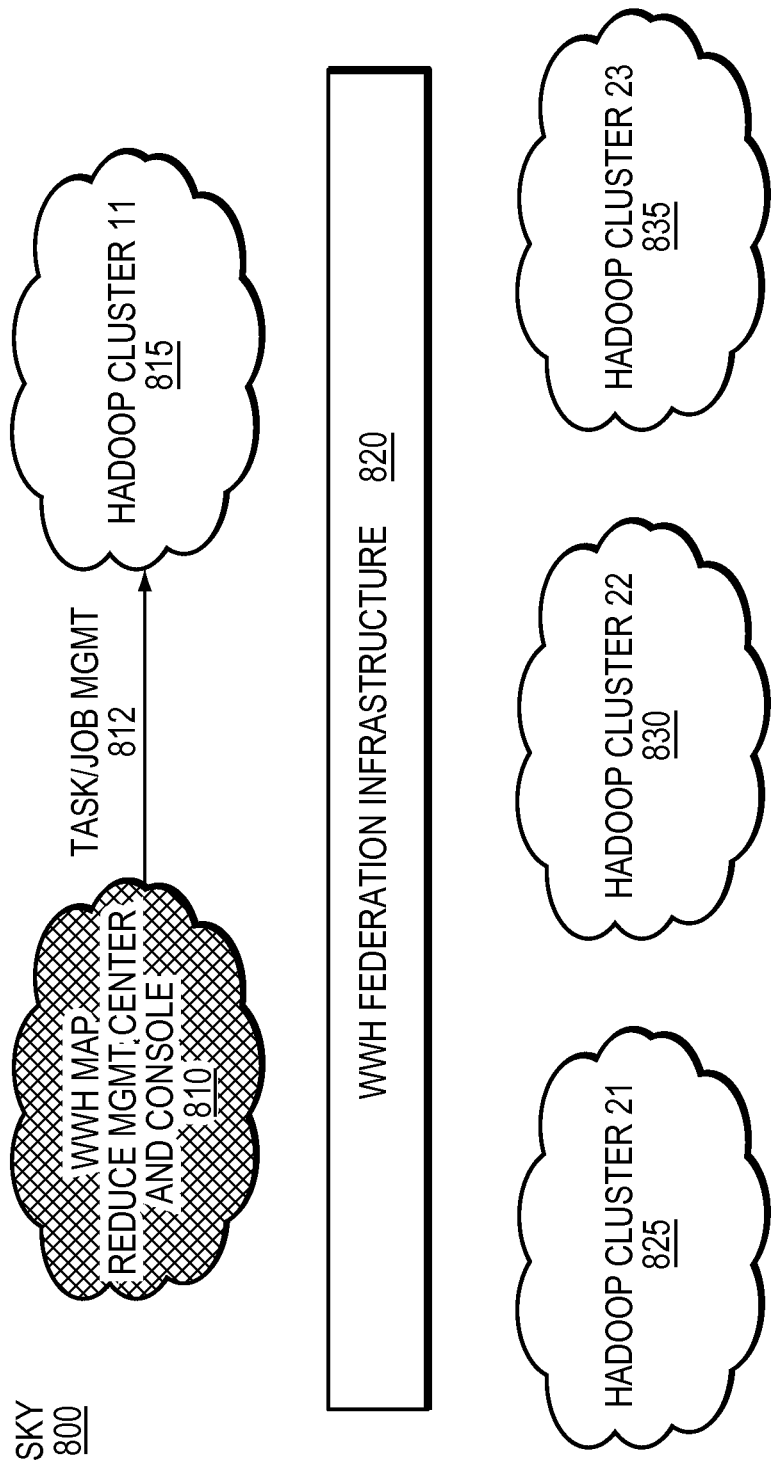
FIG. 8 is an alternative simplified illustration representing a WWH FS Management Tool Center, in accordance with an embodiment of the present disclosure.

Refer now to the example embodiment of FIG. 8, which illustrates a WWH FS management tool center. Sky 800 has 5 clouds and WWH Federation infrastructure 820. WWH Map reduce management center and console 810 is able to send map reduce commands and perform task/job management 812 with hadoop cluster 815. WWH Map reduce management center and console 810 is able to issue tasks to 825, 830, and 835 through WW Federation Infrastructure 820.

Figure 9:
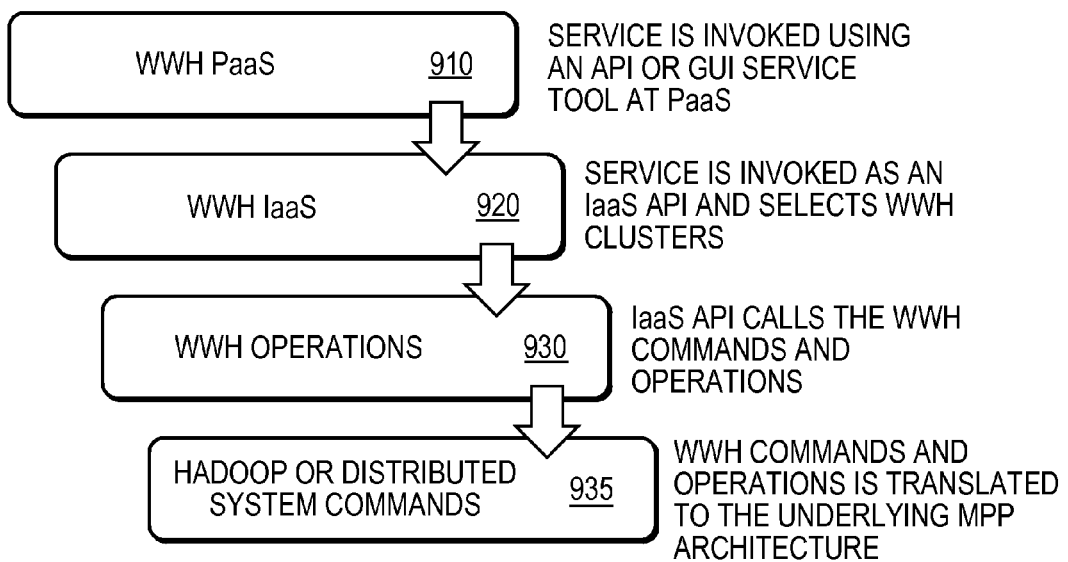
FIG. 9 is a simplified illustration of WWH PaaS and IaaS Layers, in accordance with an embodiment of the present disclosure.

Refer now to the example embodiment of FIG. 9 which illustrates sample Platform as a Service (PaaS) and Infrastructure as a Service (IaaS) Layers. WWH PaaS 910 is invoked using an API or GUI service tool at the PaaS level. WWH IaaS 920 service is invoked as an IaaS API and selects WWH clusters. WWH Operations 930 is called by the IaaS API with commands and operations. Hadoop or Distributed System Commands 935 are translated from the WWH commands to the underlying MPP architecture.

Figure 10:
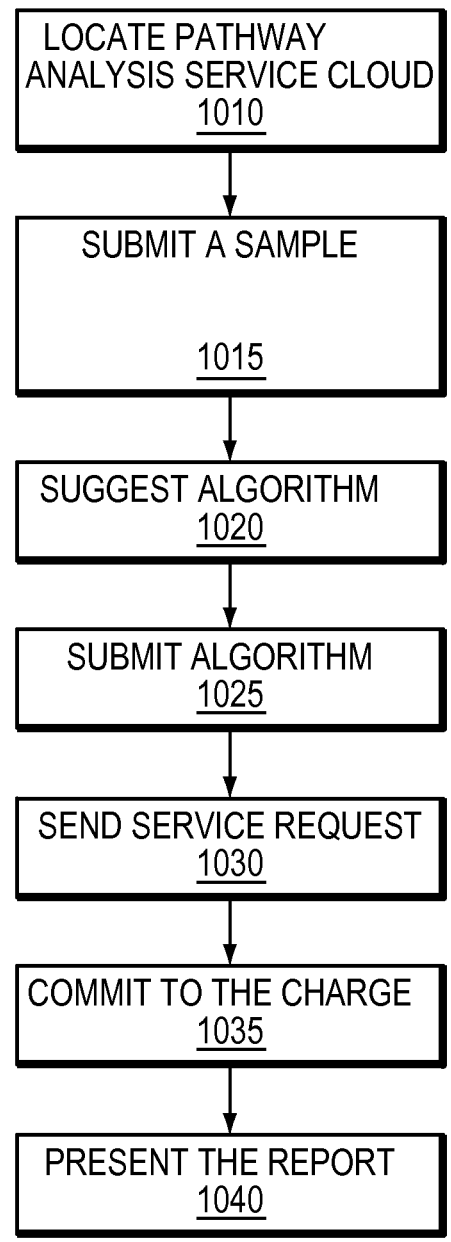
FIG. 10 is a simplified method for invoking a service tool from a cloud, in accordance with an embodiment of the present disclosure.

Refer now to the example embodiment of FIG. 10, which illustrates invoking a service tool from a cloud. A user locates the pathway analysis service cloud using service locator tool (step 1010). The user submits a digitalized pathology sample from the producer cloud using a job data submission data tool (step 1015). Job submission tool suggests user to run many available algorithms as jobs (step 1020). User submits a proprietary algorithm to be run the data using a job submission tool (step 1025). A service request is sent to the pathway analysis cloud, which in turn presents an invoice with service charges (step 1030). User commits to the service charges in the service management tool, and waits for analysis report/outcome (step 1035). Visualization tool presents the report. User can opt to re-run the job with different algorithm to verify results (step 1040).

Figure 11:
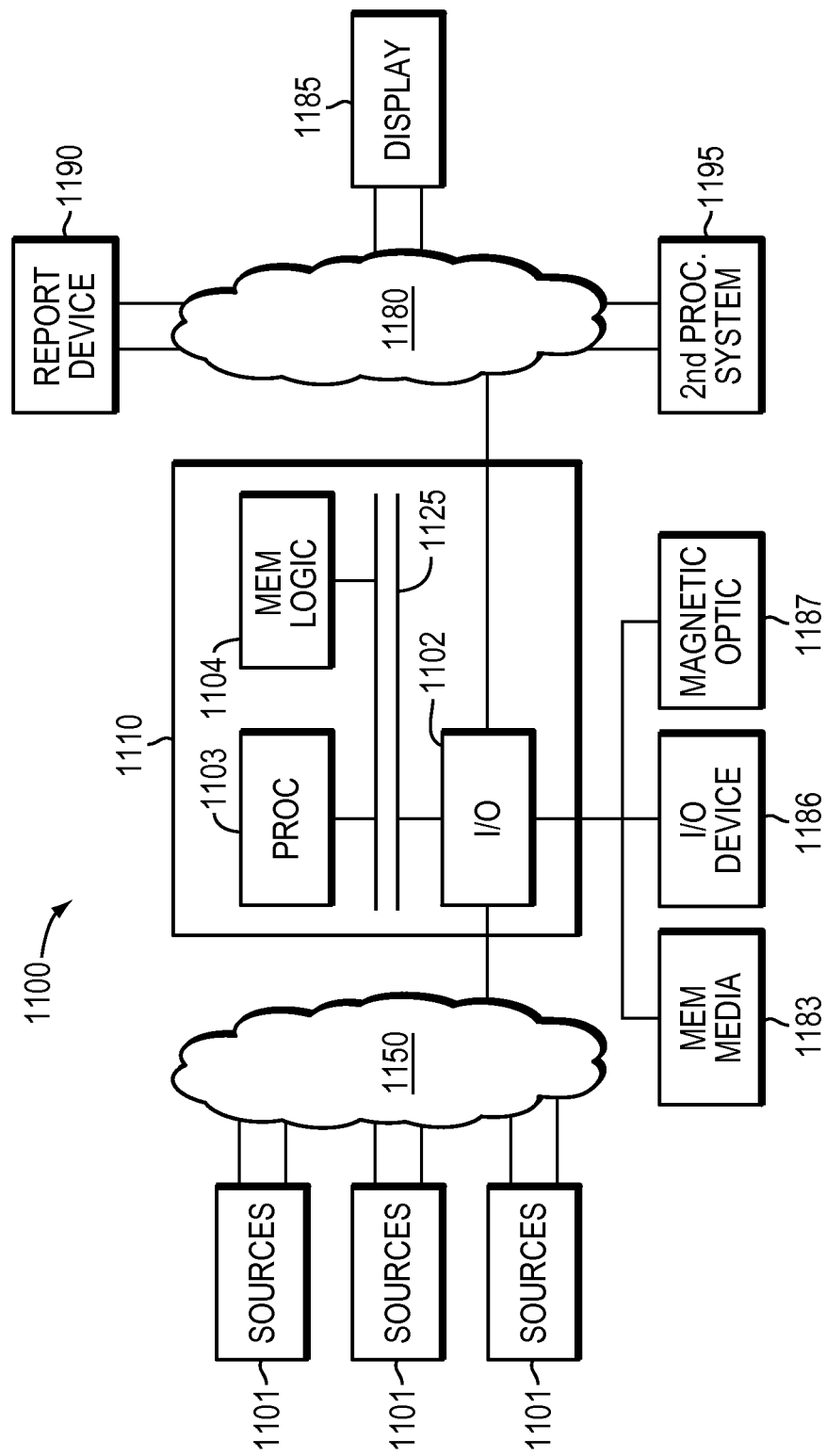
FIG. 11 is an example of an embodiment of an apparatus that may utilize the techniques described herein, in accordance with an embodiment of the present disclosure.
Figure 12:
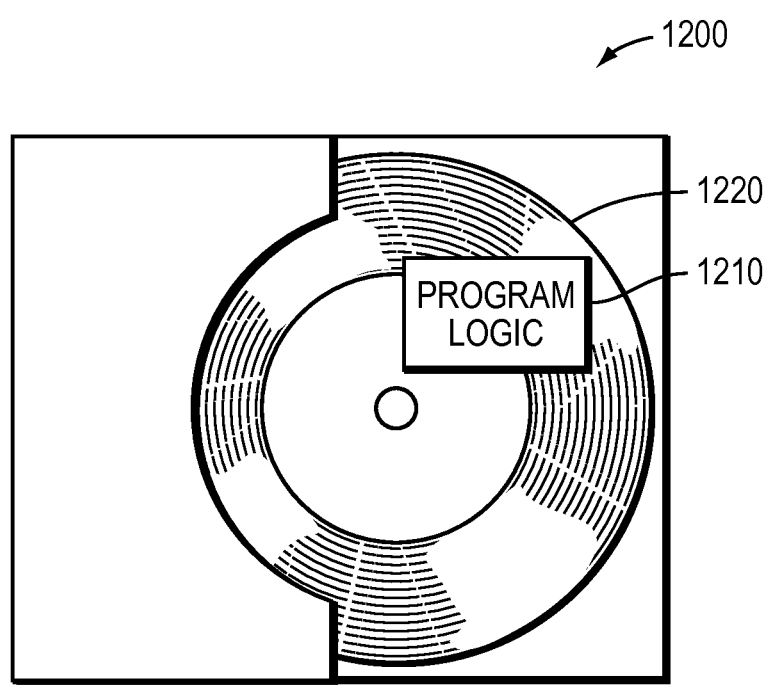
FIG. 12 is an example of an embodiment of a method embodied on a computer readable storage medium that may utilize the techniques described herein, in accordance with an embodiment of the present invention.

The methods and apparatus of this invention may take the form, at least partially, of program code (i.e., instructions) embodied in tangible media, such as floppy diskettes, CD-ROMs, hard drives, random access or read only-memory, or any other machine-readable storage medium. When the program code is loaded into and executed by a machine, such as the computer of FIG. 10, the machine becomes an apparatus for practicing the invention. When implemented on one or more general-purpose processors, the program code combines with such a processor 1003 to provide a unique apparatus that operates analogously to specific logic circuits. As such a general purpose digital machine can be transformed into a special purpose digital machine. FIG. 11 shows Program Logic 1134 embodied on a computer-readable medium 1130 as shown, and wherein the Logic is encoded in computer-executable code configured for carrying out the reservation service process of this invention and thereby forming a Computer Program Product 1100. The logic 1034 may be the same logic 1040 on memory 1004 loaded on processor 1003. The program logic may also be embodied in software modules, as modules, or as hardware modules.

Figure 7:
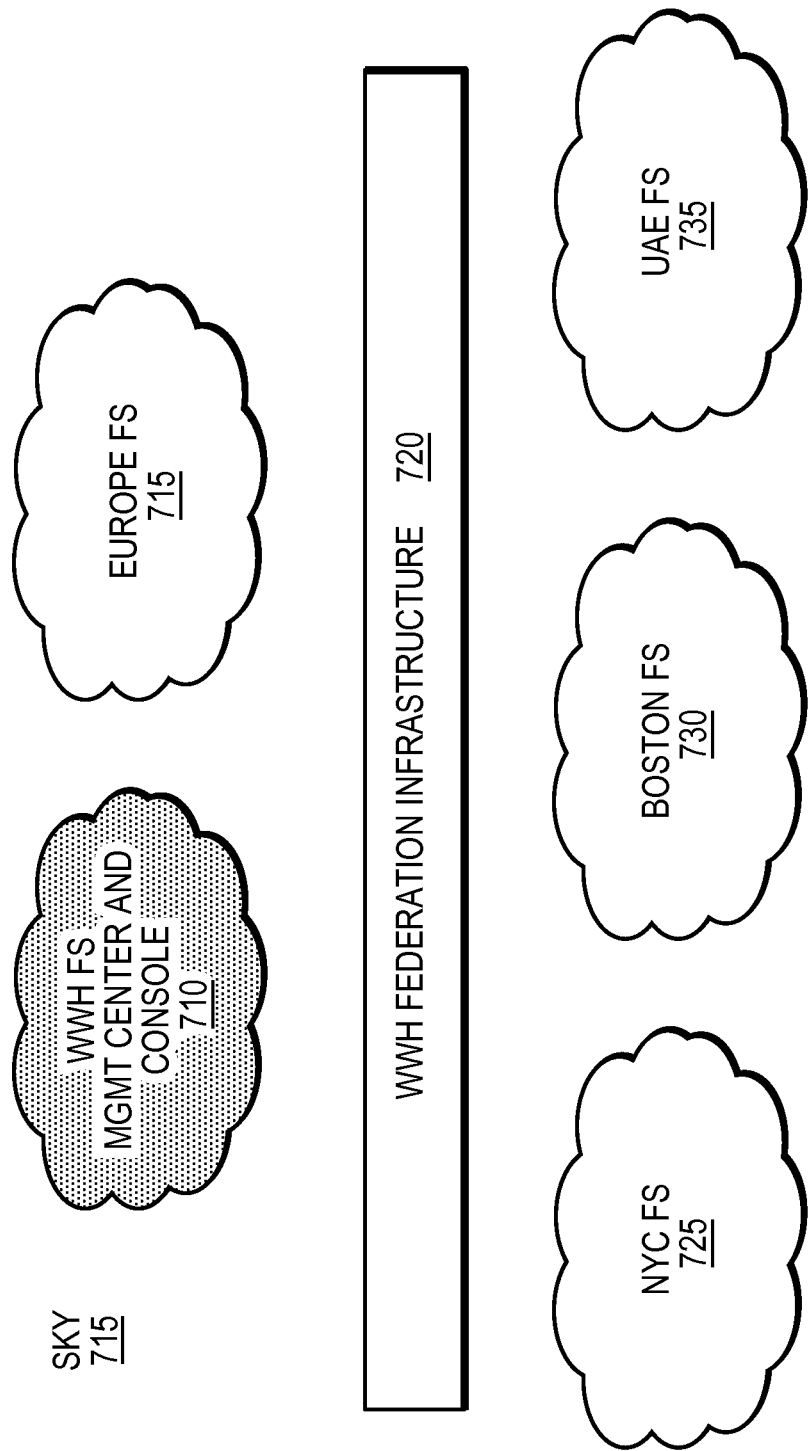
FIG. 7 is a simplified illustration representing a WWH FS Management Tool Center, in accordance with an embodiment of the present disclosure.

The logic for carrying out the method may be embodied as part of the system described below, which is useful for carrying out a method described with reference to embodiments shown in, for example, FIG. 7 and FIG. 8. For purposes of illustrating the present invention, the invention is described as embodied in a specific configuration and using special logical arrangements, but one skilled in the art will appreciate that the device is not limited to the specific configuration but rather only by the claims included with this specification.

Although the foregoing invention has been described in some detail for purposes of clarity of understanding, it will be apparent that certain changes and modifications may be practiced within the scope of the appended claims. Accordingly, the present implementations are to be considered as illustrative and not restrictive, and the invention is not to be limited to the details given herein, but may be modified within the scope and equivalents of the appended claims.

What is claimed is:

1. An apparatus comprising:
a co-location module enabled to operate on one or more processors, wherein the co-location module is configured to co-locate big data storage clouds to enable streamlined information flow between the big data storage clouds,
wherein the big data storage cloud comprises at least one resource selected from a group consisting of compute resources and storage resources,
wherein the co-locating minimizes the distance between big data storage cloud including minimizing the distance between the resources of the big data storage clouds,
wherein an information infrastructure layer enables the big data storage clouds to communicate between themselves, wherein the information infrastructure stores metadata about the big data storage clouds;
wherein the information infrastructure layer is enabled to allow a cloud of the big data storage clouds to subscribe to information from another of the big data storage clouds wherein the infrastructure layer notifies a subscribed cloud when information to which it is subscribed is modified, and
wherein the information infrastructure layer is enabled to allow a cloud of the big data storage clouds to publish information for consumption by another of the big data storage clouds to the infrastructure layer; wherein job and task trackers communicatively coupled to the infrastructure layer monitor execution of one or more jobs in one or more of the big data storage clouds.

2. The apparatus of claim 1 further comprising:
an integrating module enabled to operate on one or more processors, wherein the integrating module is configured to integrate information transfer flow between the big data storage clouds through the use of rest interfaces.

3. The apparatus of claim 2 further comprising:
a vertically integration module enabled to operate on one or more processors, wherein the integrating module is configured to vertically integrate the big data storage clouds.

4. The apparatus of claim 3 further comprising:
A federation module enabled to operate on one or more processors, wherein the federation module is configured to federate the big data storage clouds.

5. The apparatus of claim 4 further comprising:
an ensurance module enabled to operate on one or more processors, wherein the ensurance module is configured to ensure any GRC compliance and service methodology is located on a dedicated cloud.

6. The apparatus of claim 5 further comprising:—
a data analysis module enabled to operate on one or more processors, wherein the data analysis module is configured for analysis based on streamlined information flow between the clouds.

7. A computer program product comprising:
a non-transitory computer readable medium encoded with computer executable program code, the code configured to enable the execution of:
co-locating big data storage clouds to enable streamlined information flow between the big data storage clouds,
wherein the big data storage cloud comprises at least one resource selected from a group consisting of compute resources and storage resources,
wherein the co-locating minimizes the distance between big data storage cloud including minimizing the distance between the resources of the big data storage clouds,
wherein an information infrastructure layer enables big data storage clouds to communicate between themselves via the information infrastructure layer wherein the information infrastructure stores metadata about the big data storage clouds,
wherein the information infrastructure layer is enabled to allow a cloud of the big data storage clouds to subscribe to information from another of the big data storage clouds wherein the infrastructure layer notifies a subscribed cloud when information to which it is subscribed is modified, and
wherein the information infrastructure layer is enabled to allow a cloud of the big data storage clouds to publish information for consumption by another of the big data storage clouds to the infrastructure layer; wherein job and task trackers communicatively coupled to the infrastructure layer monitor execution of one or more jobs in one or more of the big data storage clouds.

8. The computer program product of claim 7 the code further configured to enable the execution of:
integrating information transfer flow between the big data storage clouds through the use of rest interfaces.

9. The computer program product of claim 8 the code further configured to enable the execution of:
vertically integrating the big data storage clouds.

10. The computer program product of claim 9 the code further configured to enable the execution of:
federating the big data storage clouds.

11. The computer program product of claim 10 the code further configured to enable the execution of:
ensuring any GRC compliance and service methodology is located on a dedicated cloud.

12. The computer program product of claim 11 wherein data analysis is based on streamlined information flow between the big data storage clouds.

13. A computer implemented method for managing big data clouds comprising:
- co-locating big data storage clouds to enable streamlined information flow between the big data storage clouds,
  - wherein the big data storage cloud comprises at least one resource selected from a group consisting of compute resources and storage resources,
  - wherein the co-locating minimizes the distance between big data storage cloud including minimizing the distance between the resources of the big data storage clouds,
  - wherein an information infrastructure layer enables big data storage clouds to communicate between themselves via the information infrastructure layer wherein the information infrastructure stores metadata about the big data storage clouds;
  - wherein the information infrastructure layer is enabled to allow a cloud of the big data storage clouds to subscribe to information from another of the big data storage clouds wherein the infrastructure layer notifies a subscribed cloud when information to which it is subscribed is modified, and
  - wherein the information infrastructure layer is enabled to allow a cloud of the big data storage clouds to publish information for consumption by another of the big data storage clouds to the infrastructure layer; wherein job and task trackers communicatively coupled to the infrastructure layer monitor execution of one or more jobs in one or more of the big data storage clouds.

14. The method of claim 13 further comprising:
integrating information transfer flow between the big data storage clouds through the use of rest interfaces.

15. The method of claim 14 further comprising:
vertically integrating the big data storage clouds.

16. The method of claim 15 further comprising:
federating the big data storage clouds.

17. The method of claim 16:
ensuring any GRC compliance and service methodology is located on a dedicated cloud.

18. The method of claim 16 wherein data analysis is based on streamlined information flow between the big data storage clouds.

19. The method of claim 16 wherein big data meta information is passed between the big data storage clouds.

20. The computer program product of claim 10 the code further configured to enable the execution of:
passing big data meta information between the big data storage clouds.

* * * * *